US011589898B2

United States Patent
Roychowdhury

(10) Patent No.: US 11,589,898 B2
(45) Date of Patent: *Feb. 28, 2023

(54) METHOD AND DEVICE FOR CONTROLLED DELIVERY OF MEDICAL DEVICES

(71) Applicant: Cogentix Medical, Inc., Minnetonka, MN (US)

(72) Inventor: Suranjan Roychowdhury, Minnetonka, MN (US)

(73) Assignee: Cogentix Medical, Inc., Minnetonka, MN (US)

( * ) Notice: Subject to any disclaimer, the term of this patent is extended or adjusted under 35 U.S.C. 154(b) by 445 days.

This patent is subject to a terminal disclaimer.

(21) Appl. No.: 16/713,512

(22) Filed: Dec. 13, 2019

(65) Prior Publication Data

US 2020/0121362 A1    Apr. 23, 2020

Related U.S. Application Data

(63) Continuation of application No. 14/920,521, filed on Oct. 22, 2015, now Pat. No. 10,537,363.

(60) Provisional application No. 62/069,597, filed on Oct. 28, 2014.

(51) Int. Cl.
| | | |
|---|---|---|
| A61B 17/34 | (2006.01) | |
| A61N 1/05 | (2006.01) | |
| A61B 90/11 | (2016.01) | |

(52) U.S. Cl.
CPC ...... *A61B 17/3468* (2013.01); *A61B 17/3403* (2013.01); *A61B 90/11* (2016.02); *A61B 2017/3407* (2013.01); *A61B 2017/3409* (2013.01); *A61N 1/0551* (2013.01)

(58) Field of Classification Search
None
See application file for complete search history.

(56) References Cited

U.S. PATENT DOCUMENTS

| | | | |
|---|---|---|---|
| 3,457,922 A | 7/1969 | Ray | |
| 4,139,011 A | 2/1979 | Benoit et al. | |
| 5,116,345 A | 5/1992 | Jewell et al. | |
| 5,741,291 A | 4/1998 | Yoo | |
| 8,216,211 B2* | 7/2012 | Mathis | A61B 90/36 606/1 |
| 8,801,664 B1* | 8/2014 | Perry | A61B 17/3403 604/116 |

(Continued)

FOREIGN PATENT DOCUMENTS

| | | |
|---|---|---|
| CN | 101829016 A | 9/2010 |
| DE | 3108766 A1 | 9/1982 |
| KR | 200404886 Y1 | 1/2006 |

OTHER PUBLICATIONS

Extended European Search Report received for European Patent Application No. 19209418.3, dated Feb. 4, 2020, 6 pages.

(Continued)

*Primary Examiner* — Shaun L David
(74) *Attorney, Agent, or Firm* — TraskBritt

(57) ABSTRACT

A device that uses an anatomic landmark or fiduciary point to establish a point of origin for device orientation in space is provided. The device controls the direction and depth of delivery of a needle, wire, trocar or cannula utilized for diagnostic or therapeutic intervention. The device guides the percutaneous delivery of a needle, wire, trocar or cannula to a target spatial location on or within tissue.

20 Claims, 19 Drawing Sheets

(56) References Cited

U.S. PATENT DOCUMENTS

| | | | |
|---|---|---|---|
| 2001/0027271 A1 | 10/2001 | Franck et al. | |
| 2002/0010479 A1* | 1/2002 | Skakoon | A61N 1/0534 606/130 |
| 2002/0138068 A1 | 9/2002 | Watson et al. | |
| 2003/0055436 A1* | 3/2003 | Daum | A61B 34/20 606/130 |
| 2003/0135241 A1 | 7/2003 | Leonard et al. | |
| 2004/0260312 A1* | 12/2004 | Magnusson | A61B 17/3403 606/129 |
| 2005/0182420 A1* | 8/2005 | Schulte | A61N 1/0539 606/130 |
| 2006/0089626 A1* | 4/2006 | Vlegele | A61B 17/3494 606/1 |
| 2006/0100501 A1* | 5/2006 | Berkel | A61B 17/3403 600/415 |
| 2007/0149947 A1* | 6/2007 | Byrum | A61M 39/0208 604/288.04 |
| 2008/0200798 A1* | 8/2008 | Eklund | A61B 90/11 600/414 |
| 2009/0036745 A1* | 2/2009 | Bonadio | A61B 17/3423 600/208 |
| 2009/0112084 A1* | 4/2009 | Piferi | A61N 1/0529 600/421 |
| 2009/0143638 A1 | 6/2009 | Keogh et al. | |
| 2010/0234726 A1 | 9/2010 | Sirimanne et al. | |
| 2010/0292724 A1* | 11/2010 | Ravikumar | A61B 17/29 606/205 |
| 2011/0118710 A1* | 5/2011 | Begemann | A61B 90/11 606/1 |
| 2011/0196205 A1* | 8/2011 | Hathaway | A61B 17/3423 600/201 |
| 2012/0283545 A1 | 11/2012 | Kuck et al. | |
| 2013/0030408 A1* | 1/2013 | Piferi | A61M 25/007 604/523 |
| 2013/0096570 A1* | 4/2013 | Solar | A61B 90/11 606/108 |
| 2013/0190809 A1* | 7/2013 | Vidlund | A61B 17/0057 606/213 |
| 2013/0197534 A1* | 8/2013 | Lauderbaugh | A61B 17/3403 606/108 |
| 2014/0018822 A1* | 1/2014 | Main | A61B 17/2909 606/130 |
| 2014/0128881 A1* | 5/2014 | Tyc | A61B 18/1492 606/20 |
| 2016/0007979 A1* | 1/2016 | Bhagat | A61B 90/50 604/175 |
| 2016/0113678 A1 | 4/2016 | Roychowdhury | |

OTHER PUBLICATIONS

International Search Report and Written Opinion dated Jan. 6, 2016 in connection with International Patent Application No. PCT/US2015/056836, 7 pages.
Extended European Search Report dated Mar. 19, 2018 in connection with European Patent Application No. 15855436.0, 6 pages.
European Communication pursuant to Article 94(3) EPC for European Application No. 19209418.3, dated Jan. 20, 2021, 3 pages.

* cited by examiner

METHOD AND DEVICE FOR CONTROLLED DELIVERY OF MEDICAL DEVICES

CROSS REFERENCE OF RELATED APPLICATIONS

This application is a continuation of U.S. patent application Ser. No. 14/920,521, filed Oct. 22, 2015, now U.S. Pat. No. 10,537,363, issued Jan. 21, 2020, which claims the benefit of U.S. Provisional Patent Application No. 62/069,597, filed Oct. 18, 2014, each of which is incorporated by reference herein, in the entirety and for all purposes.

FIELD OF THE INVENTION

The present invention relates generally to a method and device for the controlled delivery of medical devices. More specifically, the present invention relates to a device for controlling the percutaneous delivery of needles, fine wires, electrodes, trocars or cannulas to a target location in a patient.

BACKGROUND OF THE INVENTION

Physicians like neurologists and urologists, physiatrists, physical therapists, chiropractors, and other medical providers have used nerve and muscle stimulation to treat a variety of ailments. These medical providers have used various methods of neurostimulation and neuromodulation such as implanted electrical and optical devices and external electrical, magnetic and ultrasonic devices for treatments such as deep brain stimulation for Parkinson's disease and electronic muscle stimulation (EMS) and transcutaneous electrical nerve stimulation (TENS) for muscle and joint rehabilitation as well as chronic pain. Urologists and obstetrician/gynecologists have used a form of TENS for pelvic floor stimulation to treat urge incontinence, urinary frequency, non-obstructive urinary retention, interstitial cystitis, chronic pelvic pain, anal incontinence and other pelvic neuromuscular disorders.

Transcutaneous stimulators, i.e., stimulators which do not physically penetrate the skin surface, are less invasive than percutaneous and implantable stimulators. However, transcutaneous stimulators often require higher current levels than percutaneous and implantable stimulators. Higher current levels can cause irritation and discomfort when used for extended periods. Also, since transcutaneous stimulators stimulate on the skin surface, their target site usually covers a large area. Thus, transcutaneous stimulators may not be highly effective for direct nerve stimulation. This is especially true for stimulation targets that are deep to the skin surface and that may be shielded by overlying hard tissue.

More typically, providers use implantable stimulators when there is a need for direct nerve stimulation or continuous stimulation. Implantable stimulators can free a patient from the need for constant and frequent manual treatment. However, implantable stimulators can cause mild discomfort, and often cause more severe implant-site pain.

Percutaneous stimulators provide direct nerve stimulation without the invasiveness of an implant. During treatment, a conducting needle is inserted to provide electrical stimulation to a target nerve. The needle is electrically connected to a controller by a series of leads, often bound together at one end as a cable that connects to the controller. When positioned properly, the needle (which includes a receiver/electrode assembly) stimulates the tibial nerve thereby modulating nerve activity in the sacral plexus. Modulation or interruption of sacral nerve activity is useful in the treatment of the pelvic heath disorders enumerated above.

However, the needle must be precisely and accurately positioned to achieve the maximum heath benefit. There are currently no devices that facilitate or guide accurate percutaneous delivery of a needle, wire, trocar or cannula to a target spatial location on or within tissue that can be utilized by both medical personnel and patients.

Therefore, what is needed is a device that uses an anatomic landmark or fiduciary point to establish a point of origin for device orientation in space. What is also needed is a device that can control the direction and depth of delivery of the needle, wire, trocar or cannula that is part of the diagnostic or therapeutic intervention.

BRIEF SUMMARY OF THE INVENTION

The problems associated with conventional means of delivering and guiding a needle to an anatomic site are addressed by the present invention.

In certain aspects the present invention, precisely and accurately guides the percutaneous delivery of a needle, wire, trocar or cannula to a target spatial location on or within tissue.

In other aspects, the delivery device uses an anatomic landmark or fiduciary point to establish a point of origin for device orientation in space.

In other aspects the present invention controls the direction and depth of the delivery and placement of the needle, wire, trocar or cannula on or into tissue.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Unless defined otherwise, all technical and scientific terms used herein have the same meaning as is commonly understood by one of skill in the art to which this invention belongs.

Figure 1:
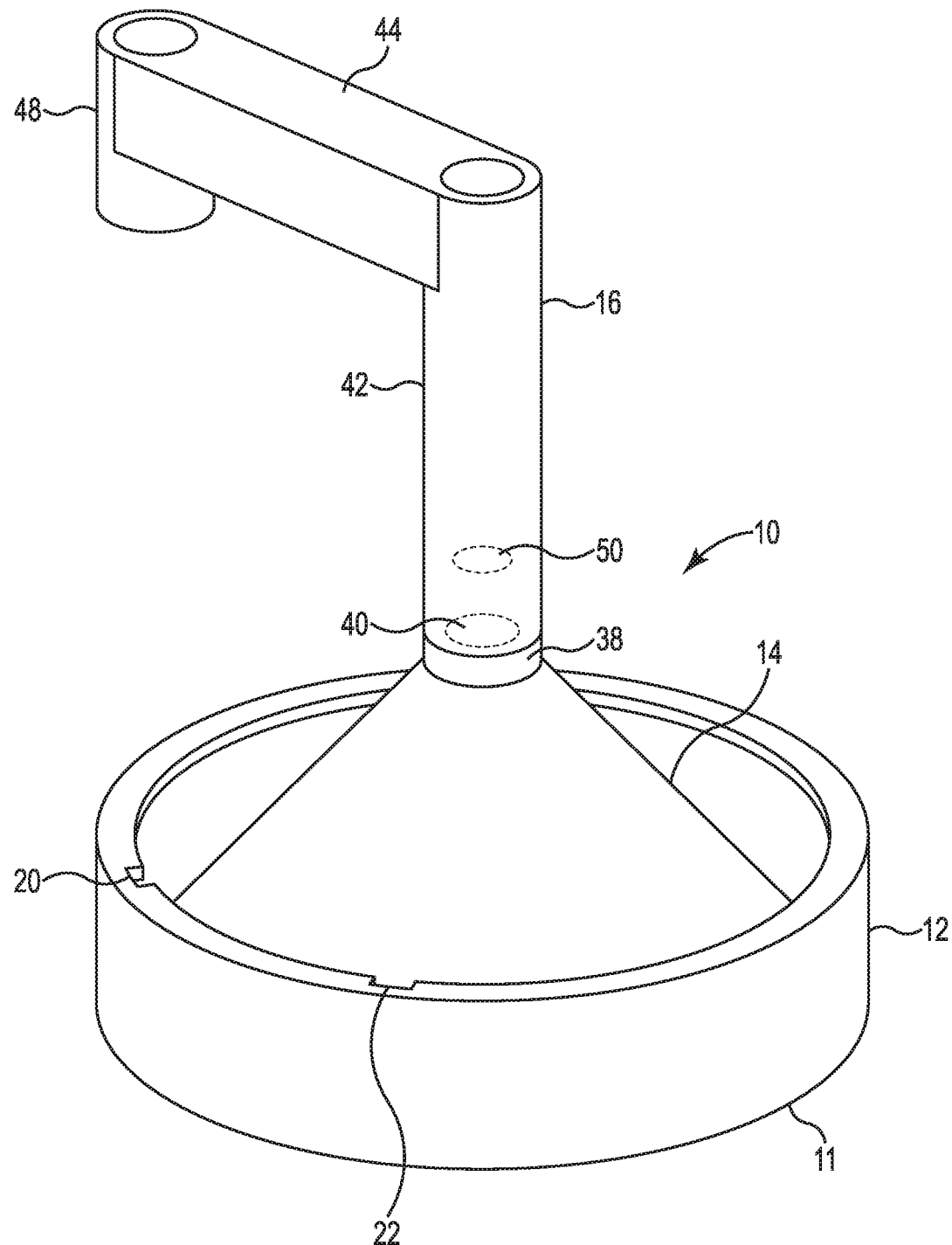
FIG. 1 is a perspective view of an exemplary delivery device in accordance with the invention.
Figure 2A:
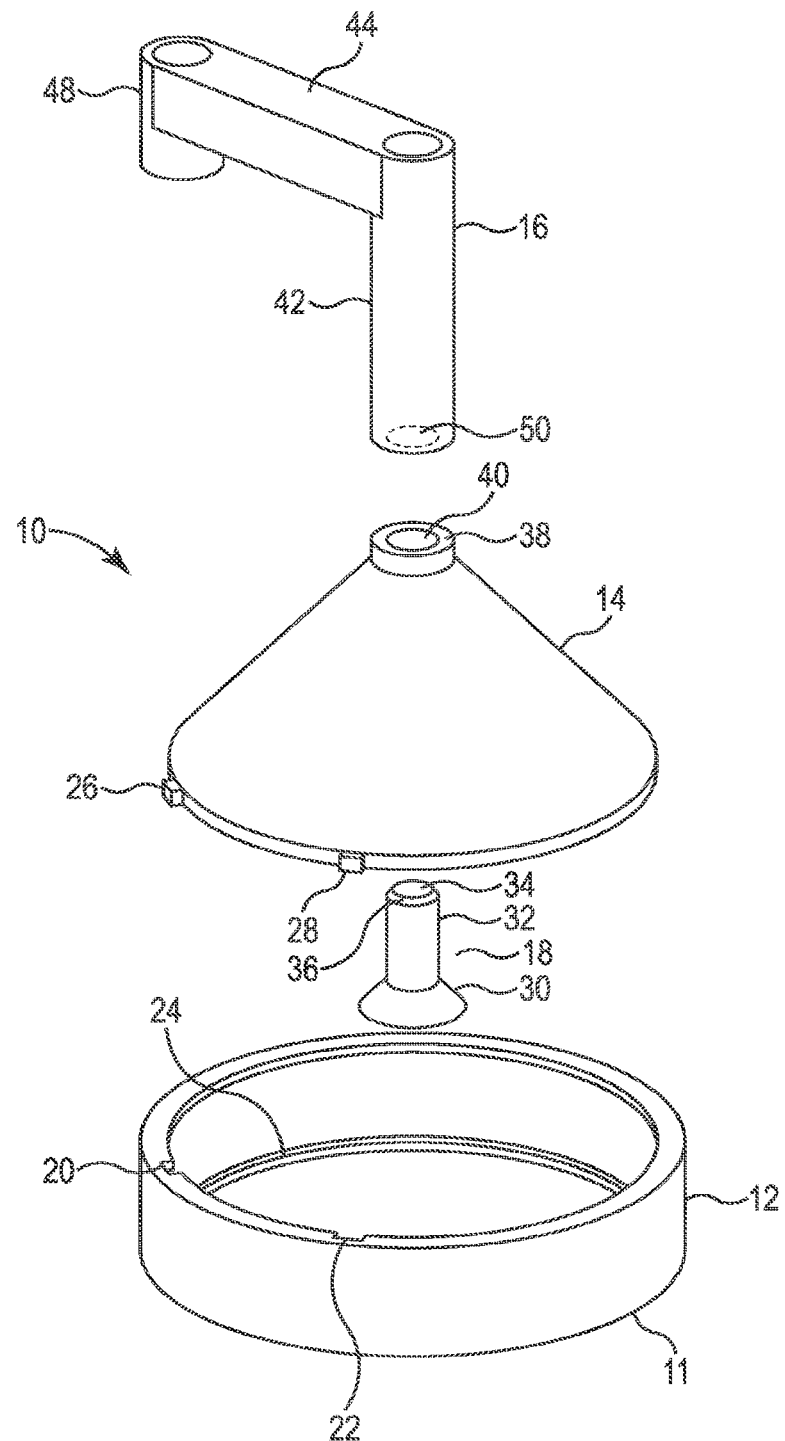
FIG. 2A is an exploded view of the exemplary device illustrated in FIG. 1.
Figure 2B:
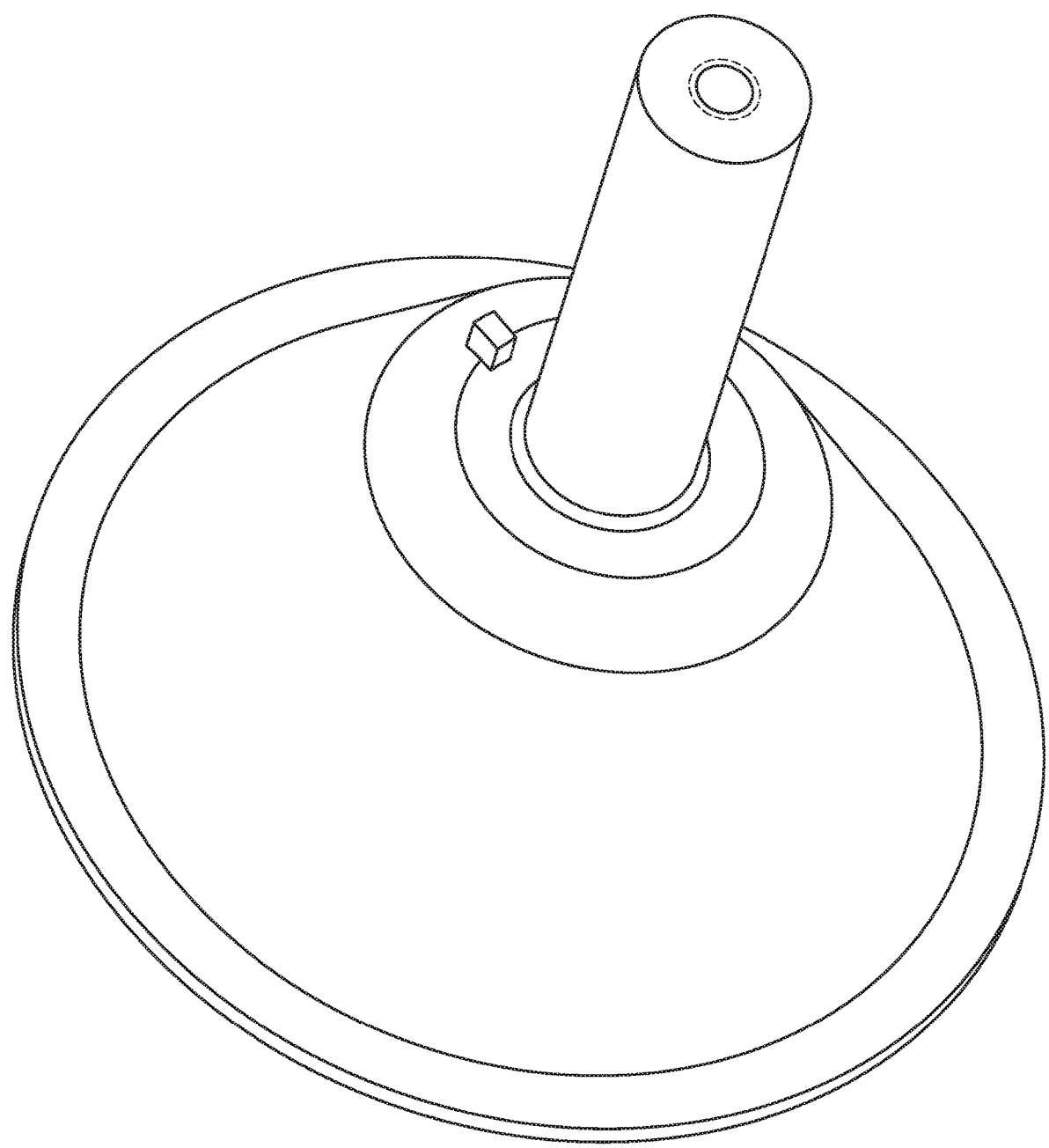
FIGS. 2B through 2E show various aspects of the exemplary device illustrated in FIG. 2A and FIG. 1.
Figure 2C:
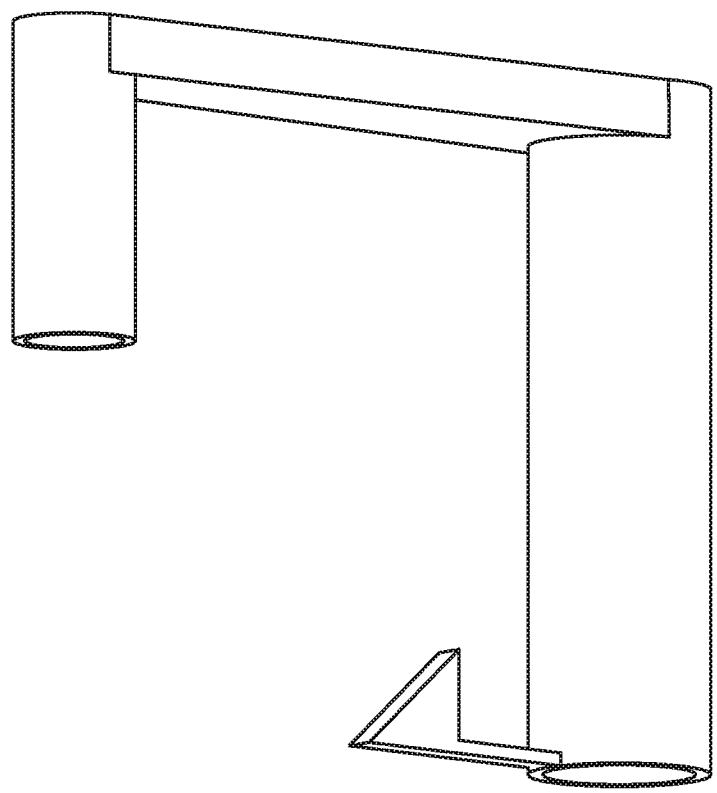
Figure 2D:
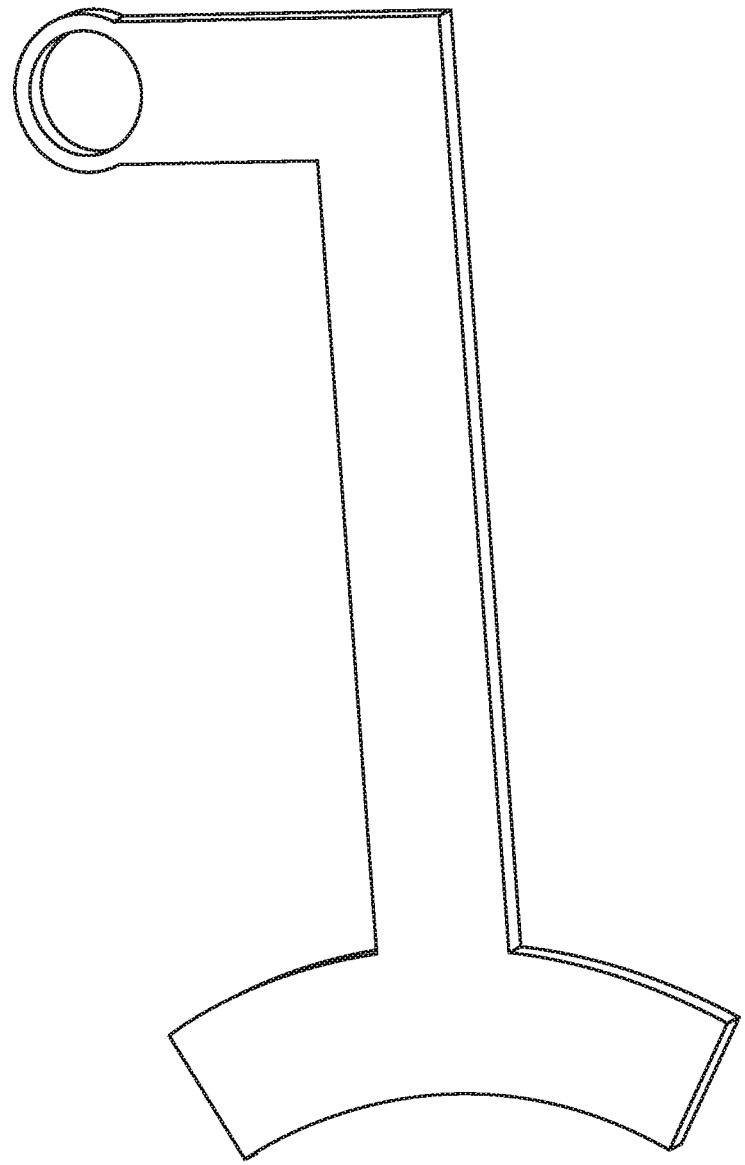
Figure 2E:
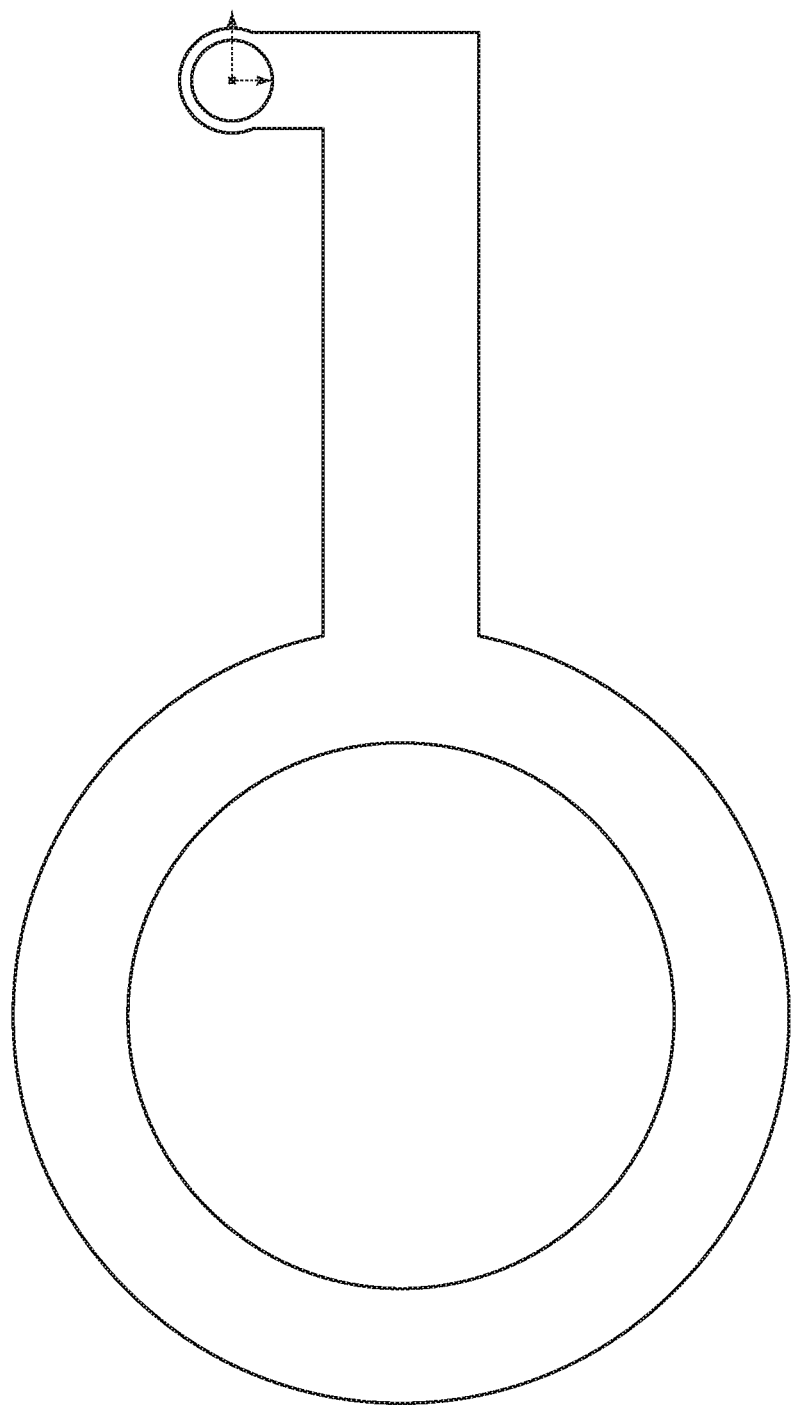

Referring now to FIGS. 1-2E the delivery device 10 in accordance with the invention broadly includes circular positioning ring 12, rotational element 14, directional element 16 and coupling mechanism 18.

Circular positioning ring is configured to circumscribe the medial malleolus, the bony prominence on the inner side of the ankle formed by the lower end of the tibia, at a preferred height. Circular positioning ring 12 includes one or more vertical receiving channels 20, 22 operably coupled to lower horizontal receiving channel 24. Cone-shaped rotational element 14 includes one or more flanges 26, 28 that are received by vertical receiving channels 20, 22 in mating relationship and operably engage with lower horizontal receiving channel 24. A manual rotational force applied to rotational element 14 will cause flanges 26, 28 to travel in lower horizontal receiving channel 24 until a stop is encountered, causing the rotational element to cease rotation at that position, with the possible additional feature of being locked into the circular ring. Rotational element 14 includes a cap portion 38 having an internal threaded lumen 40.

Circular positioning ring includes a base 11. Base 11 may incorporate the use of a sheet or ring of adhesive tape to removably secure the device 10 over the medial malleolus while in use. In alternative aspects of the invention a band or collar (not shown) may extend from the circular positioning ring 12 and circumscribe the surface of the foot, ankle and heel such that the entire device 10 assembly is centered on the medial malleolus. The band or collar may be held in place by fastening means known to those of skill in the art such as Velcro, adhesives, mechanical fasteners and combinations thereof.

Coupling mechanism 18 includes cone-shaped base 30 and shaft 32. In operation, cone-shaped base 30 is configured to be positioned externally over the medial malleolus. Shaft 32 may be integrally formed with or threadably received by base 30. If threadably received by base 30, shaft may be dimensioned such that the outer diameter of shaft 32 is less that the inner diameter of threaded lumen 40. Shaft 32 includes a needle, or needle guide and driver device, receiving lumen therethrough 34 and a threaded top portion 36. In one aspect of the invention, threaded top portion 36 is threadably received by threaded cap portion 38 operably coupling rotational element 14 with coupling mechanism 18.

Directional element 16 broadly includes vertical shaft 42, adjustable positioning arm 44 and guide tube 48. Vertical shaft includes a lumen 50 whose inner diameter is greater than the outer diameter of cap portion 38. Lumen 50 is pivotably received by cap portion 38. Those of skill in the art will appreciate that the lumen 50 may extend the length of shaft 42 or in other embodiments may be slightly greater than or equal to the vertical depth of cap portion 38.

Adjustable positioning arm 44 includes a right angle adjustable construction. To accommodate different patient anatomies, adjustable positioning arm 44 may be adjusted to a plurality of different acute angles, preferably from 30-60 degrees offset from the longitudinal axis of shaft 42, by a ratcheting mechanism (not shown).

Guide tube 48 is operably coupled to adjustable positioning arm 44. Guide tube 48 operates to position a thin gauge, non-hypodermic needle to the target location near the tibial nerve, which enables the neurostimulation therapy to be delivered. Referring now to FIGS. 3A-5 various aspects of guide tube geometry are illustrated.

Guide tube 48 operably receives a PTNS needle advance device 60 as best seen in FIGS. 3A-5. The PTNS needle advancement device enables the controlled advancement and delivery of a needle. In one aspect for the delivery of percutaneous tibial nerve stimulation (PTNS) therapy, the PTNS needle advance device 60 is designed to linearly and controllably advance a PTNS needle electrode through the surface of the skin of the lower leg proximate the medial malleolus to a target depth within the tissue to enable the clinically effective delivery of tibial neuromodulation.

Figure 3A:
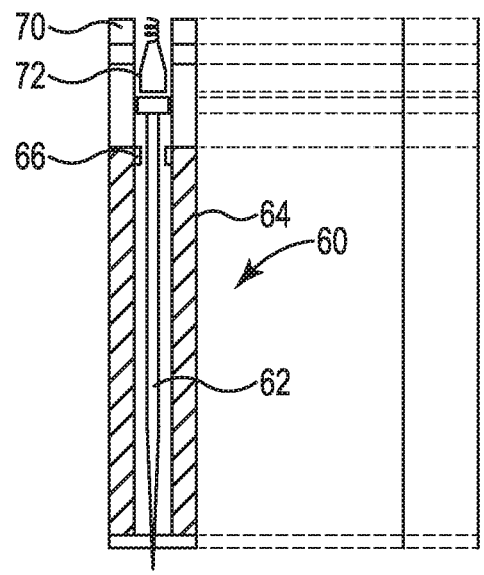
FIG. 3A is a side view of a needle advancement device in accordance with the invention.
Figure 3B:
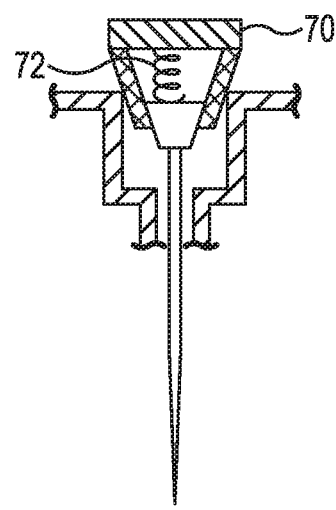
FIG. 3B is a side detailed view of the needle advancement device of FIG. 3A.

As best seen in FIGS. 3A and 3B one aspect of a PTNS needle advancement device is illustrated. Needle advance device 60 broadly includes acupuncture needle 62 housed within cylindrical sheath 64. The needle advance device 60 includes the ability to translate the acupuncture needle 62 linearly through the inner diameter (ID) of the sheath or tube. Cap 70 of the needle advance device 60 fits over the proximal end of the cylindrical sheath 64. Cap 70 includes a double-headed piston with one piston head that has a diameter greater than the I.D. of the guide tube and another piston head that has a diameter that is less than the I.D. of the guide tube. The length of the piston shaft, which also has an O.D. smaller than the I.D. of the guide tube, between the two piston heads determines the maximum length of advancement of the piston through the I.D. or lumen of the guide tube. The piston is propelled within the cap by means of spring 72. Those of skill in the art will appreciate that other means of propulsion may be incorporated into the device such as hydraulic, percussive, magnetic, electromagnetic, compressed fluids and the like. A locking mechanism 66 may be incorporated into the cap 70 or into the guide tube/needle holder element 48 to prevent undesired needle translation or movement within the cylindrical sheath 64. Cap 70 is rotatably or threadably received on cylindrical sheath 64. Spring 72 has a spring constant that allows spring to advance needle 62 as rotational or other force is applied by cap 70. The locking mechanism 66 may be contained within a single component or may be contained in separate components of the controlled advancement and delivery device. Locking mechanism 66 may be a simple interference fit of a removable component that is insertable between the ID of the cap (or the guide tube/needle holder) and the OD of the needle. When the locking component is in place, the interference fit keeps the needle from moving freely. Once it is removed, the needle is free to move within the guide tube or cap plus guide tube construct.

Figure 4:
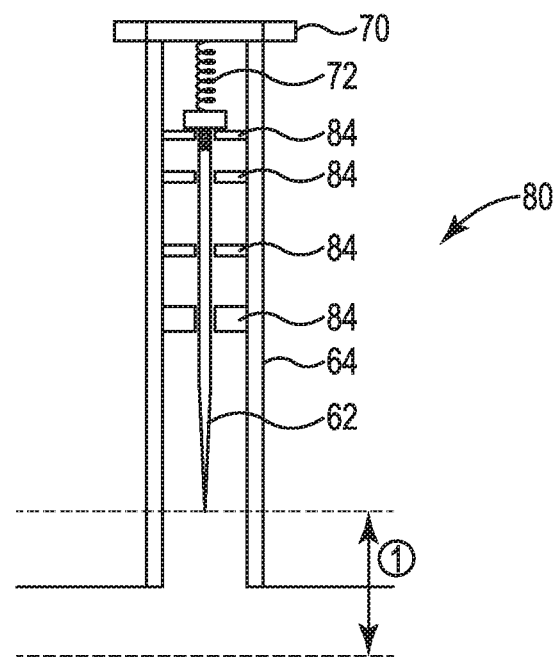
FIG. 4 is a side view of one aspect of a needle advancement device in accordance with the invention.

Referring now to FIG. 4, with like elements being labeled with like reference numerals, one aspect of a controlled advancement and delivery device 80 for a PTNS needle electrode is illustrated. A 34 gauge acupuncture needle 62 is received in a cylindrical sheath 64 of uniform or varying cross section area. The cylindrical sheath 64 may be opaque and includes inner cross-sectional dimensions larger than the maximum outer cross-sectional dimension of the acupuncture needle along its entire length or along only a portion of its length. In one aspect of the controlled advancement and delivery device for a PTNS needle electrode 80, the 34 gauge acupuncture needle 62 is placed in a cylindrical sheath 64 with a uniform circular cross-section. The sheath 64 has an inner diameter that is larger than the maximum outer diameter of the acupuncture needle. Tabs 84 are interposed between the outer surface of the acupuncture needle and the inner surface of the cylindrical sheath and serve to lock and/or controllably advance the position of the needle by means of a frictional or interference fit. Tabs 84 may be juxtaposed in a parallel relationship or may alternatively be staggered. Tabs 74 may be broken or retracted which in turn allows the acupuncture needle to advance freely within the cylindrical sheath 64 to the next set of tabs 74. The tabs can be broken or retracted via the linear advance of a cap feature that progresses along the outside of the sheath/needle holder element. This is a feasible design but not our first choice due to cost reasons.

Figure 5:
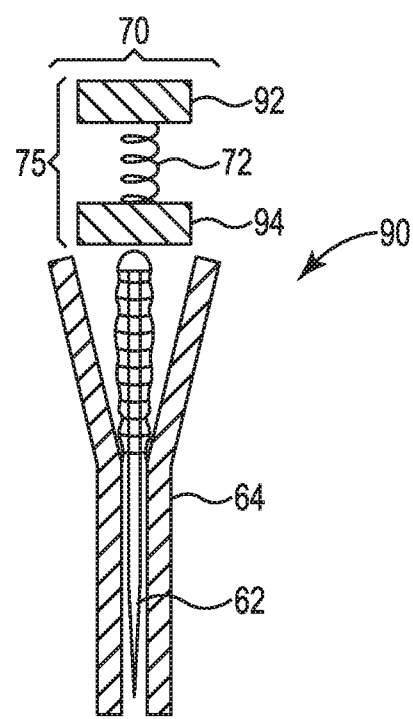
FIG. 5 is a side view of another aspect of a needle advancement device in accordance with the invention.

Referring now to FIG. 5 another aspect of a controlled advancement and delivery device 90 for a PTNS needle electrode 62 is illustrated. Cap 70 including a controlled advancement mechanism 75 fits over one end of the cylindrical sheath 64. Controlled advancement mechanism 75 broadly includes first and second piston heads 92, 94 and spring 72 interposed therebetween or between cap 70 and first piston head 92. First piston head 92 has a diameter greater than the I.D. of the cylindrical sheath 64 and second piston head 94 has a diameter that is less than the I.D. of the cylindrical sheath 64. The length of the piston shaft, i.e., the length extending from the proximal tip of the first piston head 92 to the distal tip of the second piston head 94, which also has an O.D. smaller than the I.D. of the cylindrical sheath 64, between the first and second piston heads determines the maximum length of advancement of the piston through the I.D. or lumen of the cylindrical sheath 64. The first and/or second piston head may be propelled within cap 70 by means of spring 72. Those of skill in the art will appreciate that other means of propulsion may be employed such as hydraulic, percussive, magnetic, electromagnetic, compressed fluids and the like. In one aspect the double headed piston 92, 94 may be propelled by compressing spring 72, which is then allowed to elongate in stages, driving the second and or first and second piston heads forward in stages. The second and/or first and second piston heads thus advance in a controlled fashion until the outer diameter of the piston head cannot pass the point of interference or the smaller I.D. of the cylindrical sheath 64. Those of skill in the art will appreciate that the piston is a unitary double headed construction, and both heads undergo movement under the action of the propulsive mechanism, which acts against the first piston head and causes the entire unit to move forward. The piston head with the diameter that is smaller than the I.D. of the cylindrical sheath 64 is in contact with the head of the acupuncture needle, ensuring that the movement of the double headed piston also results in linear and controlled advancement of the acupuncture needle to a desired depth. The cap or the outer telescoping head also incorporates a means to specify the maximum distance of advancement of the piston and, thus, of the needle electrode that is driven by the piston. The maximum distance of advancement required for the accurate positioning of the needle electrode for PTNS can be determined from anatomical measurements; for example, it can be based on the medio-lateral diameter of the lower calf of the human leg, just above the ankle. After the needle electrode 62 has reached the target tissue location, the cylindrical sheath 64 and the cap or telescoping outer tube 70 can be withdrawn, leaving the needle electrode accessible for making the electrical connections required to deliver PTNS.

Figure 6A:
FIGS. 6A and 6B are perspective views of one aspect of a needle advancement device in accordance with the invention.
Figure 6B:
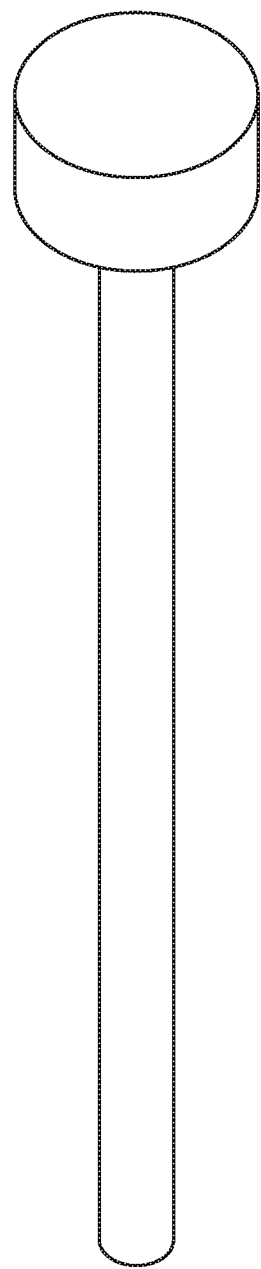

Referring now to FIGS. 6A and 6B perspective views of one aspect of a needle advancement device in accordance with the invention are illustrated.

Figure 7A:
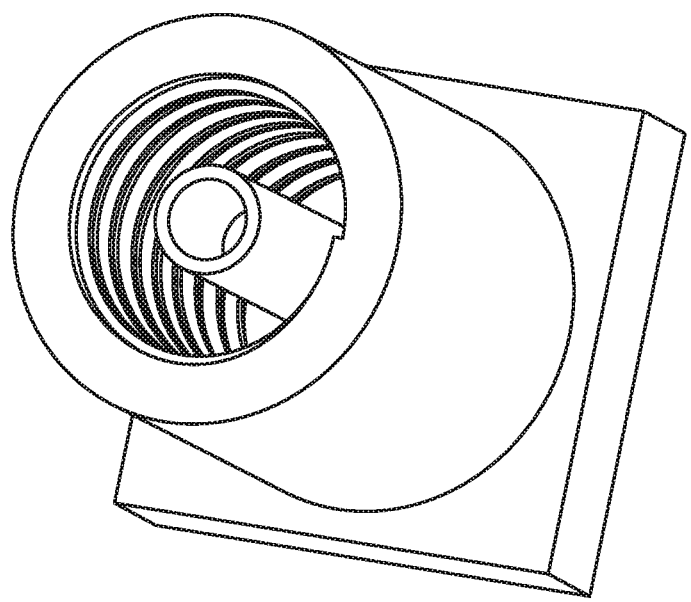
FIGS. 7A and 7B are perspective views of one aspect of a needle advancement device in accordance with the invention.
Figure 7B:

Referring now to FIGS. 7A and 7B perspective views of another aspect of a needle advancement device in accordance with the invention are illustrated.

Figure 8A:
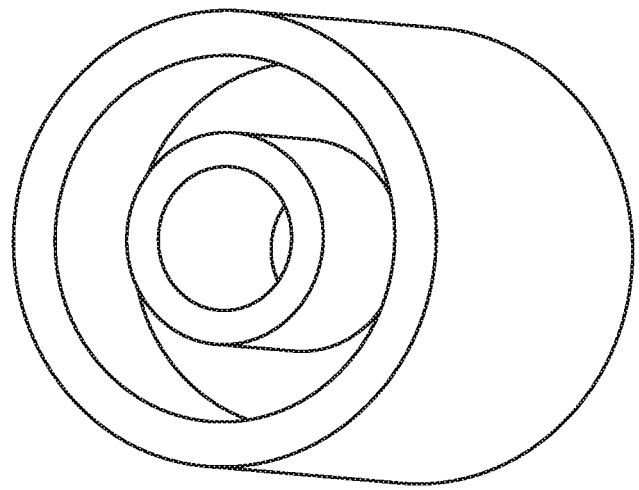
FIGS. 8A and 8B are perspective views of one aspect of a needle advancement device in accordance with the invention illustrating a wedged collar and a wedged pusher, respectively.
Figure 8B:
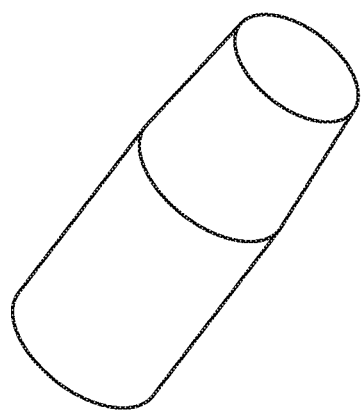

Referring now to FIGS. 8A and 8B perspective views of a further aspect of a needle advancement device in accordance with the invention illustrating a wedged collar and a wedged pusher, respectively, are illustrated.

Figure 9A:
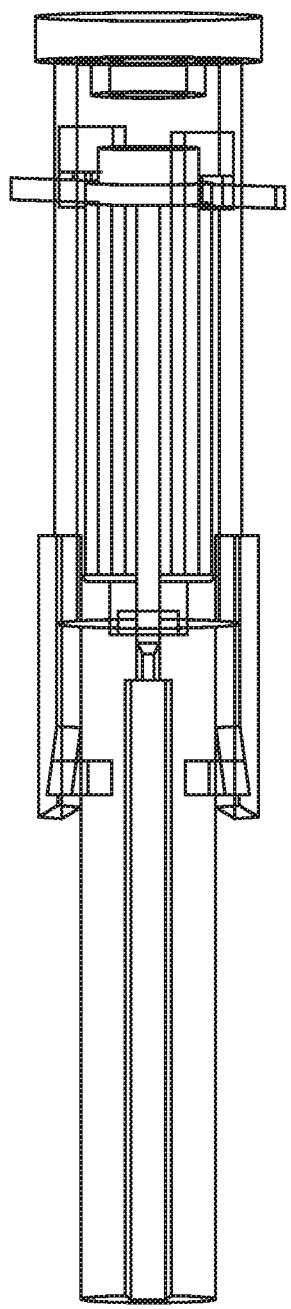
FIGS. 9A through 9E are perspective views of one aspect of a needle advancement device in accordance with the invention illustrating the complete assembly of the device in FIG. 9A and the various component parts in FIGS. 9B through 9E.
Figure 9B:
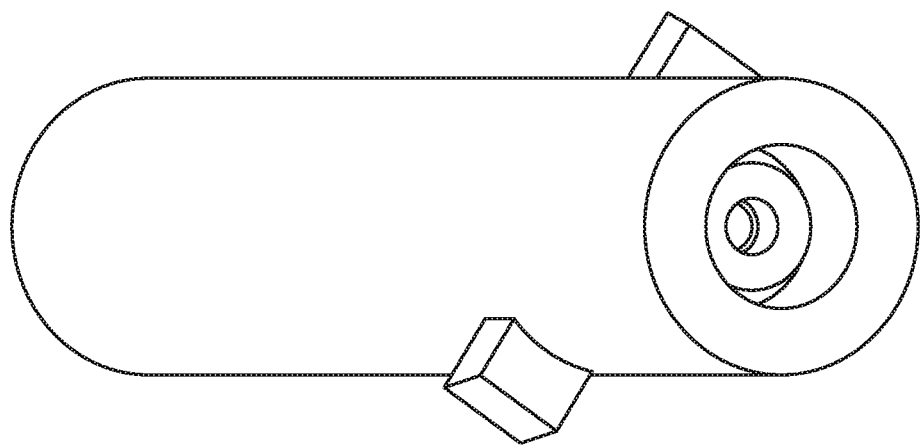
Figure 9C:
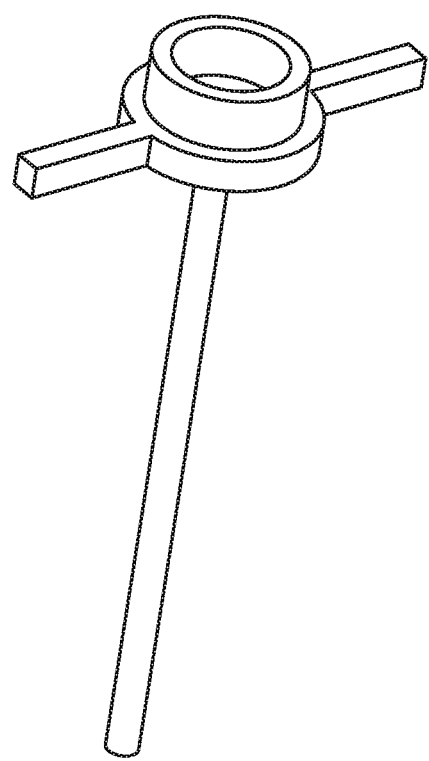
Figure 9D:
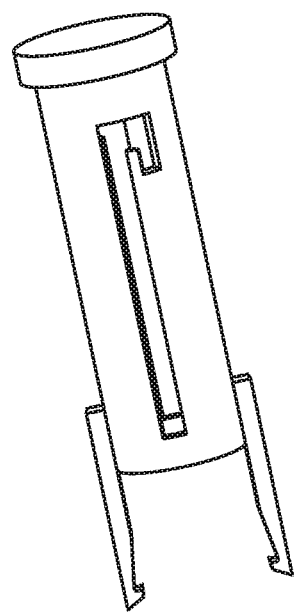
Figure 9E:
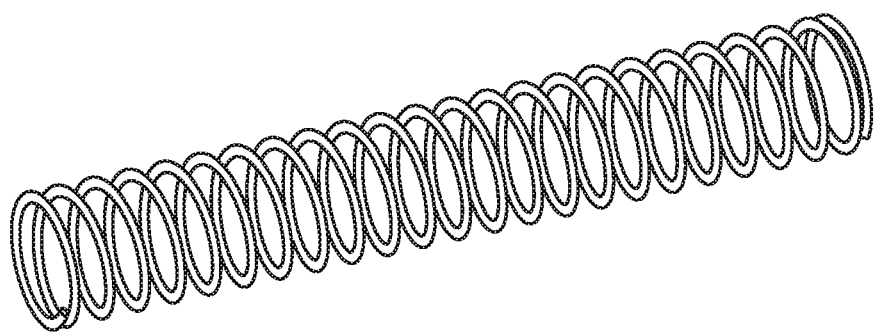

Referring now to FIGS. 9A through 9E perspective views of a further aspect of a needle advancement device in accordance with the invention are shown. Illustrated in FIG. 9A is the completed assembly of the device and the various component parts in FIGS. 9B through 9E.

Although the present invention has been described with reference to certain aspects and embodiments, those of ordinary skill in the art will appreciate that changes may be made in form and detail without departing from the spirit and scope of the invention.

What is claimed is:

1. A device that guides the percutaneous delivery of a medical device to a target spatial location on or within tissue, the device comprising:
    a circular positioning ring comprising a vertical receiving channel and a horizontal receiving channel;
    a rotational element comprising a cap and a flange received by and engaged with the vertical receiving channel and horizontal receiving channel, respectively, where the vertical receiving channel and horizontal receiving channel meet at an intersection;
    a directional element mated with the cap of the rotational element and configured to be operably coupled to the circular positioning ring; and
    a coupling mechanism comprising a base portion and a shaft having an end mated to the cap of the rotational element, where a rotational force applied to the rotational element causes the flange to rotate in the horizontal receiving channel.

2. The device of claim 1, wherein the horizontal receiving channel includes at least one stop configured to stop the flange from further rotation.

3. The device of claim 1, wherein the circular positioning ring is configured to circumscribe a medial malleolus of a patient.

4. The device of claim 3, wherein the circular positioning ring includes a base having an adhesive thereon configured to secure the device over the medial malleolus.

5. The device of claim 3, wherein a collar extends radially from the circular positioning ring, the collar configured to circumscribe a surface of a foot, an ankle or a heel to center the device on the medial malleolus.

6. The device of claim 1, wherein the coupling mechanism base portion is cone-shaped and configured to be positioned externally over a medial malleolus.

7. The device of claim 1, wherein the shaft is integrally formed with the coupling mechanism base portion.

8. The device of claim 1, wherein the shaft is threadably received by the coupling mechanism base portion.

9. The device of claim 8, wherein the cap of the rotational element includes an internal threaded lumen.

10. The device of claim 9, wherein the shaft is dimensioned such that an outer diameter is less than an inner diameter of the cap.

11. The device of claim 1, wherein the rotational element is cone-shaped.

12. The device of claim 1, wherein the rotational element includes a first outer diameter adjacent the flange and the cap includes a cap outer diameter that is less than the first outer diameter such that the rotational element tapers from the first outer diameter to the cap outer diameter.

13. The device of claim 1, wherein the coupling mechanism shaft includes a receiving lumen therethrough configured to receive a needle, needle guide, or driver device.

14. The device of claim 1, wherein the directional element includes a vertical shaft, an adjustable positioning arm and a needle guide assembly.

15. The device of claim 14, wherein the vertical shaft defines a lumen therethrough, the lumen having an inner diameter that is greater than an outer diameter of the cap.

16. The device of claim 15, wherein the lumen is configured to extend a length of the vertical shaft.

17. The device of claim 15, wherein the lumen is configured to be greater than or equal to the vertical depth of the cap.

18. The device of claim 14, wherein the adjustable positioning arm is perpendicular to a longitudinal axis of the vertical shaft.

19. The device of claim 14, wherein the adjustable positioning arm is configured to be positioned to a plurality of acute angles offset from a longitudinal axis of shaft.

20. The device of claim 14, wherein the needle guide assembly is configured to receive a needle advance device, the needle advance device configured to linearly control advancement and delivery of a needle through a surface of skin proximate the medial malleolus to a target depth within tissue.

\* \* \* \* \*